United States Patent [19]

Patel

[11] Patent Number: 4,844,883

[45] Date of Patent: Jul. 4, 1989

[54] STABILIZATION OF WINTERGREEN FLAVOR IN CHALK-BASED DENTIFRICE AND METHOD

[75] Inventor: Harshad Patel, Wembley, England

[73] Assignee: Florasynth, Inc., New York, N.Y.

[21] Appl. No.: 5,020

[22] Filed: Jan. 20, 1987

[51] Int. Cl.$^4$ .......................... A61K 7/16; A61K 9/68
[52] U.S. Cl. ........................................ 424/49; 424/48; 426/3; 426/4; 426/5; 426/6
[58] Field of Search .................... 424/48, 49; 426/3, 4, 426/5, 6

[56] References Cited

U.S. PATENT DOCUMENTS

| | | | |
|---|---|---|---|
| 1,171,392 | 2/1916 | Meier | 426/3 |
| 4,352,822 | 10/1982 | Cherukuri et al. | 426/6 |
| 4,357,355 | 11/1982 | Koch et al. | 426/6 |
| 4,378,374 | 3/1983 | Reggio et al. | 426/3 |
| 4,387,108 | 6/1983 | Koch et al. | 426/6 |
| 4,448,789 | 5/1984 | Yang | 426/3 |
| 4,497,832 | 2/1985 | Cherukuri et al. | 426/5 |
| 4,518,615 | 5/1985 | Cherukuri et al. | 426/6 |
| 4,582,707 | 4/1986 | Calabro | 426/4 |
| 4,721,620 | 1/1988 | Cherukuri et al. | 426/6 |
| 4,726,953 | 2/1988 | Carroll et al. | 426/5 |

*Primary Examiner*—Shep K. Rose
*Attorney, Agent, or Firm*—Dressler, Goldsmith, Shore, Sutker & Milnamow, Ltd.

[57] ABSTRACT

Wintergreen flavor stability in chalk-based dentifrices containing calcium carbonate as an abrasive cleaning and polishing agent is improved on storage aging by including therein a flavor-stabilizing agent that is an ester selected from the group consisting of a lower acid ester of glycerin in which the lower acid portion is derived from a saturated monocarboxylic acid having 2 to 6 carbon atoms and a lower alcohol ester of citric acid in which the lower alcohol portion is derived from an aliphatic monohydroxy alcohol having 2 to 4 carbon atoms, used singly or in combination. A stabilized wintergreeen flavor composition suitable for use in flavoring chalk-based dentifrices is disclosed, along with a method for improving the stability of the wintergreen flavor in such dentifrices.

20 Claims, No Drawings

STABILIZATION OF WINTERGREEN FLAVOR IN CHALK-BASED DENTIFRICE AND METHOD

TECHNICAL FIELD

This invention relates generally to so-called chalk-based dentifrices containing calcium carbonate as an abrasive cleaning and polishing agent and, in particular, to such chalk-based dentifrices having improved wintergreen flavor stability.

BACKGROUND OF THE INVENTION

Dentifrices contain solid abrasives that remove debris and residual stains from the teeth and polish the tooth surface. The most widely used abrasives are calcium carbonate, dibasic calcium phosphate dihydrate, anhydrous dibasic calcium phosphate, tricalcium phosphate, calcium pyrophosphate, insoluble sodium metaphosphate, hydrated alumina, and hydrated silica.

Calcium carbonate, in particular, is an economical abrasive. It is found in nature in many geological forms and is generally derived from chalk, or is prepared as a precipitate from a calcium salt solution. A particularly preferred form of calcium is precipitated chalk for use in chalk-based dentifrices. So-called chalk-based dentifrices contain calcium carbonate either alone as the principal abrasive cleaning and polishing agent, or in admixture with other dental abrasives. Reference herein to chalk-based dentifrice refers to such defined dentifrices, regardless of the source or form of calcium carbonate abrasive.

An important factor in a consumer's selection of a dentifrice is its taste or flavor, so conventionally at least one or more flavoring agents are included. Among popular dentifrice flavors are wintergreen, spearmint, peppermint, cinnamon-mint, sassafras, and anise. Wintergreen is particularly popular as a principal flavor ingredient. However, the forementioned abrasive cleaning and polishing agents typically used in dentifrices generally are known absorptive materials. Consequently, they can, and frequently do, alter the organoleptic characteristics and stability of flavors owing to physical and/or chemical interactions, and selected absorption of some of the flavoring components.

In chalk-based dentifrices, the stability of wintergreen flavors especially is adversely changed. For example, it is known from experience that methyl salicylate, the main flavor component in oil of wintergreen, degrades relatively quickly in the presence of precipitated chalk leaving behind substantially no perceptable flavor. This same instability is not observed in chalk-free dentifrices. Thus, it has not heretofore been possible to use calcium carbonate in the form of precipitated chalk as an abrasive cleaning and polishing agent in dentifrice compositions flavored with wintergreen.

Thus, there is a need for a flavor-stabilizing agent for wintergreen flavoring agents containing methyl salicylate suitable for use in dentifrices containing calcium carbonate as an abrasive cleaning and polishing agent. This invention satisfies that need and provides for such a flavor-stabilizing agent.

SUMMARY

This invention relates to stabilization of wintergreen flavor, and particularly methyl salicylate, against storage deterioration in the presence of calcium carbonate in a chalk-based dentifrice by including therein a flavor-stabilizing agent that is an ester selected from the group consisting of a lower acid ester of glycerin in which the lower acid portion is derived from a saturated monocarboxylic acid having 2 to 6 carbon atoms and a lower alcohol ester of citric acid in which the lower alcohol portion is derived from an aliphatic monohydroxy alcohol having 2 to 4 carbon atoms, used singly or in combination.

In one aspect, this invention provides a wintergreen-flavored, chalk-based dentifrice containing calcium carbonate as an abrasive cleaning and polishing agent, and having improved wintergreen flavor stability on storage aging. More particularly, the stabilization of wintergreen flavor in such chalk-based dentifrice, and particularly in aqueous dentifrices, is preferably accomplished by including a flavor-stabilizing agent that is an ester selected from the group consisting of monoacetin (glyceryl monoacetate), diacetin (glyceryl diacetate), triacetin (glyceryl triacetate), dibutyrin (glyceryl dibutyrate), tributyrin (glyceryl tributyrate), glyceryl tricaproate, triethyl citrate, tripropyl citrate, and tributyl citrate, used singly or in combination, in an amount sufficient to extend the stability of the flavoring agent.

In practicing the principles of this invention, a methyl salicylate containing wintergreen flavoring agent is stabilized in a chalk-based dentifrice by the flavor-stabilizing agent so that a wintergreen flavor is detectable and retained in an excess of about 70 percent of starting amount. The amount retained is determined by assaying the methyl salicylate content in the dentifrice by gas chromatography analysis before and after shelf storage aging the dentifrice at an elevated temperature of about 40° C. over a period of at least one week.

The flavor-stabilizing agents of this invention are normally bitter-tasting or unpleasant-tasting liquids. Surprisingly, these flavor-stabilizing agents, used singly or in combination, were found suitable as stabilizers of wintergreen flavor without imparting a bitter taste to or modifying the organoleptic character of the wintergreen flavor in the chalk-based dentifrice product. Particularly preferred flavor-stabilizing agents are diacetin, triacetin, and triethyl citrate.

Wintergreen flavoring for use as a primary flavorant in chalk-based dentifrice is selected from the group consisting of methyl salicylate and natural oil containing methyl salicylate, used singly or in combination. A particularly preferred natural oil is wintergreen oil.

Another aspect of this invention provides a stabilized wintergreen flavor composition suitable for use in a chalk-based dentifrice and having improved stability therein. A preferred flavor composition comprises from about 2 to about 50 percent by weight of a wintergreen flavoring agent selected from the group consisting of methyl salicylate and natural oil containing methyl salicylate, used singly or in combination; and from about 25 to about 98 percent by weight of flavor-stabilizing agent, as above identified. The remainder (if any) of the stabilized flavor composition comprises a flavor-modifying agent present in sufficient amount to augment or enhance the taste of the wintergreen flavor and/or a liquid water-miscible organoleptically acceptable dispersing agent present in sufficient amount to disperse the flavoring agent and the flavor-stabilizing agent in the flavored dentifrice.

In a particularly preferred embodiment, the foregoing wintergreen flavor composition is stabilized with a flavor-stabilizing agent selected from the group consisting of diacetin, triacetin, triethyl citrate, used singly or in combination.

According to a method aspect of this invention, the stability of a wintergreen flavor containing methyl salicylate is improved against storage aging in a dentifrice containing calcium carbonate and comprises the steps of providing an unflavored dentifrice vehicle containing the calcium carbonate; providing a selected wintergreen flavoring agent for the dentifrice; admixing the wintergreen flavoring agent with at least one flavor-stabilizing agent of this invention to provide a stabilized flavoring composition; and dispersing the obtained stabilized flavoring composition in the dentifrice vehicle to provide a flavored dentifrice.

In the foregoing method, a flavor-modifying agent for the flavoring agent can be provided and admixed in the stabilized flavoring composition prior to the dispersing step. Likewise, a liquid water-miscible dispersing agent, as above identified, can also be provided for dispersing the flavoring agent and the flavor-stabilizing agent and admixed in the stabilized flavoring composition prior to the dispersing step.

The flavor-stabilizing agents disclosed beneficially extend the storage stability of wintergreen flavor in chalk-based dentifrice compositions so that a substantial proportion of the detectable wintergreen flavor is retained over the intended useful shelf life of these products. In particular, the stabilization of methyl salicylate, the primary component of wintergreen flavor, by a flavor-stabilizing agent of this invention allows the use of calcium carbonate, especially in the form of precipitated chalk, as an economic principal abrasive cleaning and polishing agent in wintergreen-flavored dentifrices.

Still further benefits and advantages will become apparent to those who are skilled in the art from the detailed description of the invention, the examples, and the claims that follow.

DETAILED DESCRIPTION OF THE INVENTION

The term "chalk-based" dentifrice previously defined and as used herein defines dentifrices containing calcium carbonate as either the sole principal abrasive cleaning and polishing agent, or in admixture with other dental abrasives. The term "dentifrice" includes products in the form of aqueous compositions, such as toothpastes, dental creams, gels, and in the form of powder compositions. The term "abrasive" defines an ingredient that is capable of cleaning and polishing the surface of the teeth in the manner recognized as acceptable to those skilled in the dental arts. Preferably calcium carbonate is the principal abrasive in a chalk-based dentifrice, i.e., other abrasives, if any, are present in lesser amount.

Aqueous compositions are particularly of interest for practicing the principle of this invention. For convenience and not by way of limitation, therefore, the stabilization of wintergreen flavoring as taught herein will be discussed predominantly in connection with aqueous dentifrice compositions.

An aqueous dentifrice composition of this invention, in its simplest form, comprises water having dispersed therein calcium carbonate, a sufficient amount of wintergreen flavoring containing methyl salicylate as the primary flavorant, and a flavor-stabilizing agent that is an ester selected from the group consisting of a lower acid ester of glycerin in which the lower acid portion is derived from a saturated monocarboxylic acid having 2 to 6 carbon atoms and a lower alcohol ester of citric acid in which the lower alcohol portion is derived from an aliphatic monohydroxy alcohol having 2 to 4 carbon atoms selected from the group, used singly or in combination, present in an amount sufficient to extend the stability of the flavoring on storage aging. Preferably, the flavor-stabilizing agent is an ester selected from the group consisting of monoacetin (glyceryl monoacetate), diacetin (glyceryl diacetate), triacetin (glyceryl triacetate), dibutyrin (glyceryl dibutyrate), tributyrin (glyceryl tributyrate), glyceryl tricaproate, triethyl citrate, tripropyl citrate, and tributyl citrate. More preferably, the flavor-stabilizing agents are the glyceryl acetates, i.e., monoacetin, diacetin, and triacetin, the glyceryl butyrate, i.e., tributyrin, triethyl citrate, and tributyl citrate. Particularly preferred are diacetin, triacetin, and triethyl citrate.

For purposes of practicing this invention, a chalk-based dentifrice in which calcium carbonate is the principal or sole abrasive cleaning and polishing ingredient contains at least about 10 percent calcium carbonate. Aqueous chalk-based dentifrice contains calcium carbonate in amounts of up to about 80 percent by weight, preferably from about 25 to about 60 percent by weight, more preferably about 35 to about 50 percent by weight. The amount of total dental abrasive content in a chalk-based dentifrice is readily determinable by persons skilled in dentifrice art.

Calcium carbonate may be in the form of precipitated chalk (precipitated calcium carbonate), prepared chalk, powdered limestone, and milled marble. Precipitated chalk is preferred. Preferably, the calcium carbonate is of a particle size suited for dentifrice abrasivity, typically of a weight median diameter of less than about 40 microns.

Auxiliary dental abrasive cleaning and polishing agents can be included in a dentifrice of this invention. Suitable auxiliary abrasives include dicalcium phosphate, dihydrate, dicalcium phosphate anhydrous, tricalcium phosphate, sodium or potassium metaphosphates, tetracalcium pyrophosphate, calcium silicate, zirconium silicate, hydrated silica, such as silica xerogel and silica aerogel, hydrated alumina, and the like.

Wintergreen flavoring can be imparted to a chalk-based dentifrice using methyl salicylate alone, and by natural oils containing methyl salicylate. Exemplary natural oils that contain methyl salicylate include wintergreen oil, sweet birch oil, betula oil, and teaberry oil, used singly or in combination with one another. Methyl salicylate can be used in combination with natural oil selected from the foregoing group to enhance the organoleptic character of these oils. A particularly preferred oil is wintergreen oil.

The use of a combination of wintergreen flavoring agents is largely a matter of choice based on economics, availability of ingredients, and subjective organoleptic preferences. Those skilled in flavoring art will appreciate that the amount of flavoring sufficient to impart a detectable wintergreen flavor in a dentifrice is readily determined on the basis of taste level desired in the finished dentifrice. Thus, the amount of flavoring utilized is limited only by these aforementioned considerations, or to levels that are substantially non-irritating to the oral cavity, or as are subject to any applicable governmental regulations.

A useful level of total wintergreen flavoring agent in a chalk-based dentifrice is in an amount from about 0.02 to about 2 percent by weight, preferably from 0.5 to about 1.5 percent by weight based on methyl salicylate content in the flavored dentifrice. In a dentifrice of this invention, the desired level of flavoring is obtained by incorporating an appropriate amount of a stabilized flavoring composition of this invention into an unflavored dentifrice vehicle, as described hereinafter. The phrase "stabilized flavoring composition", as used herein, therefore, refers to such a formentioned admixture.

For purposes of practicing this invention, wintergreen flavors stabilized for use in chalk-based dentifrices are prepared as a stabilized flavor composition by admixing a selected wintergreen flavoring agent with a selected flavor-stabilizing agent of this invention prior to dispersing it in an unflavored dentifrice vehicle. It is to be understood that the unflavored vehicle contains substantially the remainder of the formula ingredients.

The preparation of dentifrices by a number of acceptable methods is well-known in the art and readily found in the dentifrice literature. See, for example, Balsam and Sagarin, Editors, *Cosmetics: Science and Technology*, second Edition, V1, published by Wiley-Interscience, 1972, and Garlen "How To Formulate A Dentifrice", *HAPPI*, V18, No. 9, pages 62–63, 65, 1981. Except for preparing the stabilizing flavoring composition as described above, the flavoring composition is included into an unflavored dentifrice vehicle in a conventional manner. Preferably, a dentifrice in paste or gel form is prepared under vacuum conditions until all ingredients are uniformly dispersed.

The flavor-stabilizing agents of this invention are oil-like liquids that can be admixed directly with methyl salicylate or natural oil containing methyl salicylate to form a homogeneous admixture. Preferably, an edible grade is utilized. See, for example, the food grade specifications for triacetin and for triethyl citrate found in the *Food Chemical Codex*, 3rd Edition, published by the National Academy Press, 1981.

A useful total amount of flavor-stabilizing agent is in the range of from about 0.1 to about 4 percent by weight, preferably 0.1 to about 2 per cent by weight, more preferably from about 0.15 to about 1.5 percent by weight, based on the finished flavored dentifrice composition.

The stabilization of wintergreen flavor is analytically determinable by assaying the methyl salicylate content of the dentifrice product prior to and at predetermined storage intervals at elevated temperatures, and subjectively evaluated by taste, as described hereinbelow.

Methods for evaluating the stability of the flavor by means of subjective taste panels are well-known techniques in the dentifrice art. A useful method is to perform paired comparisons of a selected product using a panel of about 10 persons trained in flavor evaluation. Typically, the product is packaged in a selected tube, and flavor is assessed by tasting the product expressed directly from the package and by having the same evaluator brush his or her teeth with the product. Selected multiple samples used for brushing tests are evaluated by brushing intervals between products spaced at least about 5 minutes apart. The results of the subjective method are used to correlate detectable taste at a selected assay.

Chalk-based aqueous dentifrices of this invention containing wintergreen flavoring agent stabilized with a flavor-stabilizing agent of this invention were found to retain an excess of about 70 percent of starting amount of flavor, as determined by assaying methyl salicylate content by gas chromatography analysis before and after storage aging a flavored dentifrice at a temperature of about 40 degrees C over a period of at least one week. A convenient sample size for storage aging is 100 grams of dentifrice stored in its intended package. The sample is periodically sampled for analysis over selected storage periods, starting with at least one week intervals and the degradation of methyl salicylate content from the starting amount compared.

Under these foregoing shelf storage conditions, for example, a chalk-based aqueous dentifrice (control) containing 0.5 percent by weight methyl salicylate without flavor-stabilizing agent present was found to retain less than 40 per cent of starting amount. On the other hand, when the same dentifrice vehicle contained 0.5 weight percent of either triethyl citrate or triacetin as the sole flavor-stabilizing agent under the same foregoing storage conditions, an excess of 70 percent of starting methyl salicylate content was retained. Storage of a dentifrice for one week at 40° C. was regarded to represent an accelerated storage period corresponding to about four weeks aging under ambient room temperature conditions.

A suitable method for determining methyl salicylate content comprises dissolving one gram of dentifrice in two grams methanol in a glass vial with stirring or shaking. Where the dentifrice is in the form of a paste, solution is accomplished by including about ten glass beads to assist in breaking up the paste. The resulting dissolved sample is then centrifuged, and the supernatant liquid is sampled directly for gas chromatographic analysis. The peak area ratios of methyl salicylate and internal standard, for example, butyl benzoate, are determined by gas chromatography analysis of a standard blend against the methanol extract of the sampled dentifrice, using a computing integrator, such as Pye Unichem or Data Control Limited Model 308. This same method is used to determine the percentage of methyl salicylate in a formulation even where no internal standard is included.

The foregoing gas chromatographic analysis is suitably carried out using a 2.1 meter glass packed column with 10 percent CARBOWAX ® 20 M (a polyethylene glycol having an average of about 350 oxyethylene groups available from Union Carbide Corporation, Danbury, Ct.) coated on CHROMASORB ® G support (Chemical Dynamics Corporation, South Plainfield, N.J.). A flame ionization detector is used with nitrogen as a carrier gas. All analyses are carried out at an isothermal temperature of about 220° C.

For purposes of determining the appropriate amount of flavor-stabilizing agent for a selected amount of wintergreen flavor in any given dentifrice formulation, therefore, that amount can be selected by monitoring the stability of a desired methyl salicylate content by the foregoing gas chromatography analysis.

For example, chalk-based dentifrice compositions of this invention containing one per cent by weight methyl salicylate and either one per cent triacetin or one per cent triethyl citrate as the sole flavor-stabilizing agent were found to retain an excess of about 70 percent of starting methyl salicylate content after an aging period of about 48 days. On the other hand, the same chalk-based dentifrice flavored without flavor-stabilizing agent and similarly aged degraded relatively quickly and retained less than about 70 weight percent of starting methyl salicylate content within a period of about 12 days' storage, decreasing to less than about 55 percent by about 48 days' storage. Thereafter, methyl salicylate content continued to substantially degrade in the dentifrice containing no flavor-stabilizer, resulting in no apparent detectable wintergreen taste after a period of about 90 days' storage. On the other hand, in the presence of either flavor stabilizer, an excess of 25 percent of starting amount of methyl salicylate was retained after a storage period of about 22 weeks, and a wintergreen taste was still detectable.

Substantially similar stabilizing of wintergreen flavor is found whether the flavor-stabilizing agents of this invention, and, in particular, diacetin, triacetin, and triethyl citrate, are used singly or in combination. The selection of a single flavor-stabilizing agent or the relative amounts of each in a combination, therefore, is determined by such factors as cost, the desired level of recognizable wintergreen flavor desired in the finished flavored dentifrice, as well as by the presence of flavor-modifying agents typically employed in dentifrices. For example, a combination of diacetin, triacetin, and triethyl citrate flavor-stabilizing agents is generally preferred when a flavor-modifying agent is included in the flavoring composition.

A stabilized wintergreen flavor composition suitable for use in flavoring a chalk-based dentifrice comprises a homogeneous mixture of from about 2 to about 50 percent by weight of a wintergreen flavoring agent selected from the group consisting of methyl salicylate and natural oil containing methyl salicylate, used singly or in combination, and from about 25 to about 98 percent by weight of a flavor-stabilizing agent of this invention that is an ester preferably selected from the group consisting of monoacetin (glyceryl monoacetate), diacetin (glyceryl diacetate), triacetin (glyceryl triacetate), dibutyrin (glyceryl dibutyrate), tributyrin (glyceryl tributyrate), glyceryl tricaproate, triethyl citrate, tripropyl citrate, and tributyl citrate, used singly or in combination. The remainder (if any) of the composition comprises a liquid, water-miscible organoleptically acceptable dispersing agent for the flavoring agent and the flavor-stabilizing agent. A particularly preferred stabilized wintergreen flavor composition contains diacetin, triacetin, and triethyl citrate, used singly or in combination.

The foregoing dispersing agent is preferably an adjuvant, such as propylene glycol, sorbitol, glycerine, ethanol, and polyethylene glycol, having an average number of oxyethylene groups in a range of between 4 and 20 and a molecular weight in the range of about 150 to about 900, used singly or in combination, and is present in sufficient amount to disperse the flavoring agent and the flavor-stabilizing agent in an unflavored dentifrice vehicle. Propylene glycol and glycerine are preferred dispersing agents. Suitable polyethylene glycols are sold under the designation CARBOWAX® by the Union Carbide Corporation, Danbury, CT.

The dispersing agent is organoleptically acceptable in that it does not interfere with the wintergreen flavor character, is non-toxic to humans, and generally non-irritating to oral mucosa tissues in the amount used in dentifrice formulas. Preferably, the dispersing agent is also a humectant liquid suitable as an excipient in pharmaceutical, cosmetic, and dental preparations, and can thus form a portion of the total humectant ingredient content typically present in conventional dentifrices, as discussed hereinbelow.

A stabilized wintergreen flavor composition suitable for use in flavoring chalk-based dentifrices preferably contains a mixture of methyl salicylate or a natural oil containing methyl salicylate, and a suitable amount of wintergreen flavor-modifying agent for augmenting and enhancing the perceptibility of the wintergreen taste. Suitable wintergreen flavor-modifying agents are selected from the group consisting of ethyl salicylate, menthyl acetate, peppermint oil, spearmint oil, menthol, 1-carvone, d-carvone, anethole, anise seed oil, clove oil, eugenol, sassafras oil, thyme oil, coriander oil, pimento oil, cinnamon oil, cinnamic aldehyde, caraway oil, nutmeg oil, eucalyptol, and eucalyptus oil. Preferred flavor-modifying agents are ethyl salicylate, peppermint oil, spearmint oil, and menthol. A particularly preferred flavor-modifying agent is ethyl salicylate.

In practicing the method of this invention, the flavor-modifying agents and the dispersing agents are preferably included in the stabilized wintergreen flavor composition prior to dispersing it in the unflavored dentifrice vehicle. The flavor-modifying agent and the dispersing agent can be admixed or added separately to the stabilized flavor composition.

A flavored chalk-based dentifrice of this invention may contain ingredients conventionally included in such compositions. Thus, aside from the earlier-mentioned auxiliary abrasives, the dentifrice can include binder agents, thickening agents, surface active agents, humectants, sweeteners, colors, preservatives, active therapeutic agents, as well as the mentioned flavor-modifying agents.

Humectants are typically moisturing agents that retard drying of an aqueous dentifrice vehicle. Exemplary humectants include glycerol, sorbitol, propylene glycol, and liquid polyethylene glycol, having an average number of oxyethylene groups in a range of between 4 and 20 and a molecular weight in the range of about 150 to about 900 that are also suitable as dispersing agents. A useful total amount of humectant is in the range of from about 10 per cent by weight to about 40 percent by weight in opaque dentifrices, such as chalk-based compositions.

Binder agents and thickening agents are typically natural or synthetic gums well-known in the art and are included to increase the body and viscosity of a finished aqueous dentifrice composition. Binders and thickeners are each generally used in concentrations of about 0.5 per cent to about 2 percent by weight. Exemplary binder agents include cellulose gum, sodium carboxymethylcellulose, carrageenan gum, gum tragacanth, gum karaya, Irish Moss, and sodium alginate. Exemplary thickening agents include magnesium aluminum silicate, polyvinylpyrrolidone, starch, and cross-linked acrylic acid polymers available under the designation Carbopol in various solubility grades from B. F. Goodrich Chemical Company, Cleveland, OH.

Surface active agents are well-known in the art and provide foaming action. They are typically a water-soluble non-soap or synthetic organic detergent. The surface active agents are generally present in an amount of 0.05 to about 15 percent by weight, preferably 0.5 to 5 percent by weight of the composition.

Suitable surfactants include the water-soluble salts of: higher fatty acid monoglyceride monosulfates (for example, sodium hydrogenated coconut fatty acid monoglyceride monosulfate); higher alkyl sulfates (for example, sodium lauryl sulfate); alkylarylsulfonates (for example, sodium dodecylbenzenesulfonates); and higher alkyl sulfoacetates (for example, sodium lauryl sulfoacetate). There may also be used the saturated higher aliphatic acyl amides of lower aliphatic amino carboxylic acids having 12 to 16 carbon atoms in the acyl radical and in which the amino acid portion is derived from the lower aliphatic saturated monoaminocarboxylic acids having 2 to 6 carbon atoms, such as the fatty acid amides of glycine, sarcosine, alanine, 3-aminopropanoic acid, and valine, particularly the N-lauroyl, myristoyl, and palmitoyl sarcosinate compounds. Conventional non-ionic surfactants may also be included, if desired. Popular useful surfactants include sodium lauryl sulfate, sodium lauryl sarcosinate, sodium lauryl sulfoacetate, and dioctyl sodium sulfosuccinate.

Other adjuvant ingredients, such as sweeteners, for example, soluble sodium saccharin, coloring agents, preservatives, active therapeutic agents, for example, salts that release fluoride solutions, such as sodium monofluorophosphate and sodium fluoride, and agents that enhance the anti-caries activity of fluorides, such as calcium glycerophosphate, may be added for their intended purposes and are well-known in the art.

The pH value of a chalk-based dentifrice is typically slightly basic in the range of about pH 8 to 11. Therefore, the choice of ingredients is determined by the compatibility of the ingredients under these alkaline conditions.

For purposes of illustrating preferred embodiments of the invention, the following examples of aqueous dentifrice compositions and of stabilized wintergreen flavoring compositions contain diacetin, triacetin, and triethyl citrate, used singly or in combination as the flavor stabilizers. The invention is not limited thereto, and it is to be understood that the structurally similar analogues disclosed herein are similarly useful.

EXAMPLE 1.

Chalk-Based Dentifrices Flavored With Stabilized Wintergreen

Aqueous chalk-based dentifrice compositions exemplifying the principles of the present invention are illustrated by Formulas A-I in Table I. All amounts and proportions are in percent by weight, unless otherwise indicated. A wintergreen flavor is provided in these examples by methyl salicylate, stabilized with diacetin, triacetin, triethyl citrate, used singly and in combination, as shown.

The compositions contain calcium carbonate in the form of precipitated chalk as the principal abrasive cleaning and polishing agent. The dentifrices are prepared by conventional methods in that an unflavored dentifrice vehicle is prepared and then flavored. However, the flavoring agent is first stabilized by admixing it with the flavor-stabilizing agent to provide a homogeneous stabilized flavor composition that is subsequently dispersed with the unflavored dentifrice vehicle. Flavor-modifying agent, where present, is admixed with the stabilized flavor composition prior to this dispersion.

TABLE I

| Ingredients | A | B | C | D | E | F | G | H | I |
|---|---|---|---|---|---|---|---|---|---|
| Sorbitol (70% Solution) | 30.0 | 30.0 | 30.0 | 20.0 | 20.0 | 20.0 | 20.0 | 20.0 | 15.0 |
| Glycerin | — | 4.0 | 1.0 | — | — | — | — | 1.0 | 2.0 |
| Propylene Glycol | 1.0 | — | 3.0 | 2.0 | — | 2.0 | 2.0 | 3.0 | 2.0 |
| Polyethylene Glycol 400 | — | — | — | — | 3.0 | — | — | — | — |
| Cellulose Gum | 1.4 | 1.4 | 1.4 | 1.3 | 1.3 | 1.3 | 1.3 | 1.4 | — |
| Gum Carrageenan | — | — | — | — | — | — | — | — | 1.0 |
| Magnesium Aluminum Silicate | — | — | — | — | — | — | — | — | 0.5 |
| Polyvinylpyrrolidone | 0.1 | 0.1 | 0.1 | — | — | — | — | 0.1 | — |
| Calcium Glycerophosphate | 0.1 | 0.1 | 0.1 | 0.14 | 0.14 | 0.14 | 0.14 | 0.2 | — |
| Sodium Monofluorophosphate | 0.55 | 0.45 | 0.2 | 0.76 | 0.76 | 0.76 | 0.76 | 0.8 | — |
| Sodium Fluoride | 0.15 | 0.25 | 0.1 | — | — | — | — | — | — |
| Dicalcium Phosphate, Dihydrate | — | — | — | — | — | — | — | — | 4.0 |
| Dicalcium Phosphate, Anhydrous | — | — | — | — | — | — | — | — | 8.0 |
| Calcium Carbonate | 35.0 | 40.0 | 25.0 | 25.0 | 25.0 | 35.0 | 35.0 | 45.0 | 30.0 |
| Sodium Lauryl Sulfate | 1.0 | 1.0 | 2.0 | 1.0 | 1.0 | 1.0 | 1.0 | 2.0 | 1.0 |
| Hydrated Silica | — | — | 10.0 | 10.0 | 10.0 | 3.25 | 3.25 | 3.5 | — |
| Sodium Saccharin | 0.45 | 0.45 | 0.25 | 0.3 | 0.3 | 0.5 | 0.5 | 0.25 | 0.05 |
| Titanium Dioxide | 0.5 | 0.5 | 1.2 | 1.2 | 1.15 | 0.5 | 0.5 | 1.2 | 0.5 |
| Methyl Salicylate | 1.0 | 1.0 | 1.0 | 0.5 | 0.5 | 0.3 | 0.03 | 0.02 | 2.0 |
| Triacetin | 1.0 | — | — | 0.5 | — | 0.3 | 0.1 | 1.26 | 1.5 |
| Diacetin | — | 1.0 | — | — | — | 0.03 | 0.01 | 0.01 | 1.0 |
| Triethyl- | — | — | 1.0 | — | 0.5 | 0.04 | 0.01 | 0.08 | 1.5 |

TABLE I-continued

| Ingredients | Percent In Formula | | | | | | | | |
|---|---|---|---|---|---|---|---|---|---|
| | A | B | C | D | E | F | G | H | I |
| citrate | | | | | | | | | |
| Flavor Modifying Agent | Q.S. | Q.S. | Q.S. | Q.S. | Q.S. | Q.S. | Q.S. | Q.S. | Q.S. |
| Preservative | Q.S. | Q.S. | Q.S. | Q.S. | Q.S. | Q.S. | Q.S. | Q.S. | Q.S. |
| Color | Q.S. | Q.S. | Q.S. | Q.S. | Q.S. | Q.S. | Q.S. | Q.S. | Q.S. |
| Water, Deionized, To 100% | Q.S. | Q.S. | Q.S. | Q.S. | Q.S. | Q.S. | Q.S. | Q.S. | Q.S. |

EXAMPLE 2.

Stabilized Wintergreen Flavoring Compositions

Flavoring compositions exemplifying a stabilized wintergreen flavor suitable for use in flavoring chalk-based dentifrices are illustrated by Formulas A–Q in Table II. All amounts and proportions are in percent by weight, unless otherwise indicated.

Stabilized flavoring compositions containing flavoring agent and flavor-stabilizing agent (Formulas A, J–N) are prepared by admixing the wintergreen flavoring agent, i.e., methyl salicylate or natural oil containing methyl salicylate with the flavor-stabilizing agent diacetin, triacetin, or triethyl citrate. Where a combination of the flavor-stabilizing agents is utilized, they are premixed prior to admixing with the flavoring agent for convenience. A homogeneous stabilized flavoring composition is obtained that can be incorporated into an unflavored dentifrice vehicle by dispersing it by conventional flavoring methods.

Where a flavor-modifying agent is included (Formulas B–H,P), it is admixed with the stabilized flavoring composition prior to the dispersing step. Likewise, where a dispersing agent is present (Formulas B–J, P–Q), it is admixed with the stabilized flavoring composition, along with the flavor-modifying agent, if present, or separately, prior to the dispersing step. The order in which the flavor-modifying and dispersing agent is admixed is a matter of preference or convenience.

The choice of dispersing agent, likewise, is determined by convenience and economic considerations as long as the dispersing agent is an organoleptically acceptable liquid that does not modify the organoleptic character of the wintergreen flavoring agent, is non-toxic to humans, and does not irritate the oral mucosa in the amount present in the completed dentifrice.

TABLE II

| Ingredients | Percent In Formula | | | | | | | | | | | | | | | | |
|---|---|---|---|---|---|---|---|---|---|---|---|---|---|---|---|---|---|
| | A | B | C | D | E | F | G | H | I | J | K | L | M | N | P | Q | |
| Methyl Salicylate | 2.0 | — | 2.5 | 1.25 | 10.0 | 20.0 | 20.0 | 43.5 | 43.5 | 50.0 | 50.0 | 50.0 | 50.0 | 25.0 | — | — | |
| Wintergreen Oil | — | 2.5 | — | — | — | — | 0.2 | — | — | — | — | — | — | — | — | — | |
| Betula Oil | — | — | — | — | — | — | — | — | — | — | — | — | — | — | 10.0 | — | |
| Sweet Birch Oil | — | — | — | 1.25 | — | — | — | — | — | — | — | — | — | — | — | — | |
| Teaberry Oil | — | — | — | — | — | — | — | — | — | — | — | — | — | — | — | 10.0 | |
| Ethyl Salicylate | — | 1.75 | 1.8 | — | — | 1.8 | 1.8 | 1.8 | — | — | — | — | — | — | — | — | |
| Menthol | — | .25 | — | 0.75 | — | — | — | — | — | — | — | — | — | — | — | — | |
| Spearmint Oil | — | — | — | 0.5 | 0.1 | — | — | — | — | — | — | — | — | — | 0.2 | — | |
| Peppermint Oil | — | — | — | 0.5 | 0.1 | — | — | — | — | — | — | — | — | — | — | — | |
| Triacetin | 98.0 | 85.0 | 85.4 | 85.4 | 40.2 | 67.8 | 64.5 | 44.4 | 44.4 | 40.0 | 50.0 | — | — | 25.0 | 85.0 | — | |
| Diacetin | — | — | 4.3 | 5.2 | 4.0 | 4.4 | 5.0 | 4.3 | 4.8 | 5.0 | — | 50.0 | — | 25.0 | — | — | |
| Triethyl Citrate | — | 4.0 | 5.2 | 4.3 | 5.0 | 5.2 | 4.4 | 5.2 | 6.0 | 6.0 | — | — | 50.0 | 25.0 | — | 80.0 | |
| Dispersing Agent To 100% (Comment A) | — | Q.S. | Q.S. | Q.S. | Q.S. | Q.S. | Q.S. | Q.S. | Q.S. | Q.S. | — | — | — | — | Q.S. | Q.S. | |

Comment A: Dispersing agent is a water-miscible organoleptically acceptable liquid, such as propylene glycol, polyethylene glycol 400, glycerin, or ethanol, alone or in combination, as desired.

For convenience, the dispersing agent is selected to constitute a portion of the total content of the selected humectant ingredient present in the unflavored dentifrice vehicle into which the flavoring composition is to be incorporated.

The present invention has been described with respect to preferred embodiments. Modifications and/or variations of the disclosed compositions and methods can be made without departing from the scope of the invention set forth herein. Such modifications will readily present themselves to those skilled in the art.

What is claimed is:

1. A dentifrice composition having improved wintergreen flavor stability containing
   calcium carbonate as an abrasive cleaning and polishing agent;
   a sufficient amount of wintergreen flavoring agent as a primary flavorant selected from the group consisting of methyl salicylate and natural oil containing methyl salicylate, used singly or in combination; and
   a flavor-stabilizing agent that is an ester selected from the group consisting of a lower acid ester of glycerin in which the lower acid portion is derived from a saturated monocarboxylic acid having 2 to 6 carbon atoms and a lower alcohol ester of citric acid in which the lower alcohol portion is derived from an aliphatic monohydroxy alcohol having 2 to 4 carbon atoms, used singly or in combination, present in an amount sufficient to extend the stability of said flavoring in the presence of said calcium carbonate on storage aging said flavored dentifrice, wherein said dentifrice composition is in paste, cream or gel form.

2. A dentifrice according to claim 1, wherein said calcium carbonate is selected from the group consisting of precipitated chalk, prepared chalk, powdered limestone, and milled marble.

3. A dentifrice according to claim 1, wherein said natural oil containing methyl salicylate is selected from the group consisting of wintergreen oil, sweet birch oil, betula oil, and teaberry oil, used singly or in combination.

4. A dentifrice according to claim 1, wherein said flavor-stabilizing agent is selected from the group consisting of monoacetin, diacetin, triacetin, dibutyrin, tributyrin, glyceryl tricaproate, triethyl citrate, tripropyl citrate, and tributyl citrate.

5. A dentifrice according to claim 1, wherein said selected wintergreen flavor is stabilized by said flavor-stabilizing agent so that an excess of about 70 percent of starting amount is retained as determined by assaying methyl salicylate content in said flavored dentifrice by gas chromatography analysis before and after storage aging said dentifrice at an elevated temperature of about 40 degrees C. over a period of at least one week.

6. A dentifrice according to claim 1, wherein said calcium carbonate is present in an amount of at least about 10 percent by weight.

7. A dentifrice according to claim 1, containing from about 0.02 to about 2 percent by weight wintergreen flavoring agent based on methyl salicylate content in said dentifrice.

8. A dentifrice according to claim 1, wherein said flavor-stabilizing agent is present in a total amount of from about 0.1 to about 4 percent by weight.

9. A dentifrice according to claim 1, further containing a flavor-modifying agent selected from the group consisting of ethyl salicylate, menthyl acetate, peppermint oil, spearmint oil, menthol, 1-carvone, d-carvone, anethole, anise seed oil, clove oil, eugenol, sassafras oil, thyme oil, coriander oil, pimento oil, cinnamon oil, cinnamic aldehyde, caraway oil, nutmeg oil, eucalyptol, and eucalyptus oil, present in an amount sufficient to enhance or augment the taste of said wintergreen flavor.

10. A dentifrice according to claim 9, wherein said composition further includes water, auxiliary abrasive cleaning and polishing agents, humectants, binder agents, thickening agents, surface active agents, sweeteners, colors, preservatives, and active therapeutic agents.

11. An aqueous dentifrice composition having improved wintergreen flavor stability comprising water having dispersed therein
calcium carbonate as an abrasive cleaning and polishing agent;
a sufficient amount of wintergreen flavoring agent as a primary flavorant selected from the group consisting of methyl salicylate and natural oil containing methyl salicylate, used singly or in combination; and
a flavor-stabilizing agent that is an ester selected from the group consisting of monoacetin, diacetin, triacetin, dibutyrin, tributyrin, glyceryl tricaproate, triethyl citrate, tripropyl citrate, and tributyl citrate, used singly or in combination, present in an amount sufficient to extend the stability of said flavoring in the presence of said calcium carbonate on storage aging said flavored dentifrice.

12. In a wintergreen-flavored aqueous dentifrice composition containing calcium carbonate, the improvement comprising including a wintergreen flavor-stabilizing agent that is an ester selected from the group consisting of a lower acid ester of glycerin in which the lower acid portion if derived from a saturated monocarboxylic acid having 2 to 6 carbon atoms and a lower alcohol ester of citric acid in which the lower alcohol portion is derived from an aliphatic monohydroxy alcohol having 2 to 4 carbon atoms, used singly or in combination, in an amount sufficient to extend the stability of said wintergreen flavor so that an excess of about 70 percent of starting amount is retained, as determined by assaying methyl salicylate content by gas chromatography analysis of said dentifrice before and after storage aging said flavored dentifrice over a period of at least one week at an elevated temperature of about 40 degrees C.

13. A method of improving the stability of a selected wintergreen flavoring agent containing methyl salicylate in a dentifrice containing calcium carbonate as an abrasive and polishing agent comprising the steps of:
providing an unflavored dentifrice vehicle containing said calcium carbonate,
providing said wintergreen flavoring agent,
admixing said wintergreen flavoring agent with at least one flavor-stabilizing agent that is an ester selected from the group consisting of a lower acid ester of glycerin in which the lower acid portion is derived from a saturated monocarboxylic acid having 2 to 6 carbon atoms and a lower alcohol ester of citric acid in which the lower alcohol portion is derived from an aliphatic monohydroxy alcohol having 2 to 4 carbon atoms, used singly or in combination, to provide a stabilized flavoring composition for said dentifrice, and
dispersing said obtained stabilized flavoring composition in said dentifrice vehicle to provide a wintergreen-flavored dentifrice that is in paste, cream or gel form.

14. The method according to claim 13, further including the steps of:
providing a flavor-modifying agent for said flavoring agent; and
admixing said flavor-modifying agent in said stabilized flavoring composition in the step prior to the dispersing step.

15. The method according to claim 13, further including the steps of:
providing a liquid water-miscible organoleptically acceptable dispersing agent for said flavoring agent and said flavor-stabilizing agent, selected from the group consisting of propylene glycol, sorbitol, glycerin, ethanol, and polyethylene glycol having an average number of oxyethylene groups in a range of between about 4 and about 20, and a molecular weight in the range of about 150 to about 900, used singly or in combination, and admixing said dispersing agent in said stabilized flavoring composition in the step prior to the dispersing step.

16. A dentifrice comprising calcium carbonate and a stabilized wintergreen flavor composition having improved stability therein, said dentifrice having a paste, cream or gel form, said stabilized wintergreen flavor composition comprising from about 2 to about 50 percent by weight of a wintergreen flavoring agent selected from the group consisting of methyl salicylate and natural oil containing methyl salicylate, used singly or in combination; and from about 25 to about 98 percent by weight of a flavor-stabilizing agent that is an ester selected from the group consisting of a lower acid ester of glycerin in which the lower acid portion is derived from a saturated monocarboxylic acid having 2 to 6 carbon atoms and a lower alcohol ester of citric acid in which the lower alcohol portion is derived from an aliphatic monohydroxy alcohol having 2 to 4 carbon atoms, used singly or in combination.

17. A dentifrice according to claim 16, wherein said flavor-stabilizing agent is selected from the group consisting of monoacetin, diacetin, triacetin, dibutyrin, tributyrin, glyceryl tricaproate, triethyl citrate, tripropyl citrate, and tributyl citrate.

18. A dentifrice according to claim 16, wherein said composition further includes a liquid, water-miscible organoleptically acceptable dispersing agent selected from the group consisting of propylene glycol, sorbitol, glycerin, ethanol, and polyethylene glycol having an average number of oxyethylene groups in a range of between about 4 and about 20 and a molecular weight in the range of between about 150 to about 900, used singly or in combination, present in sufficient amount to disperse said flavoring agent and said flavor-stabilizing agent in said dentifrice.

19. A dentifrice according to claim 16, wherein said composition further includes a flavor-modifying agent present in an amount sufficient to augment or enhance the taste of said wintergreen flavor useful in said dentifrice.

20. A dentifrice according to claim 19, wherein said flavor-modifying agent is selected from the group consisting of ethyl salicylate, menthyl acetate, peppermint oil, spearmint oil, menthol, l-carvone, d-carvone, anethole, anise seed oil, clove oil, eugenol, sassafras oil, thyme oil, coriander oil, pimento oil, cinnamon oil, cinnamic aldehyde, caraway oil, nutmeg oil, eucalyptol, and eucalyptus oil.

* * * * *